United States Patent [19]

Baggiolini et al.

[11] Patent Number: 5,759,533
[45] Date of Patent: Jun. 2, 1998

[54] NEUTROPHIL-ACTIVATING PEPTIDE-2

[75] Inventors: Marco Baggiolini, Berne; Kenneth John Clemetson, Bollingen; Alfred Walz, Köniz, all of Switzerland

[73] Assignees: Novartis AG, Basel; Theodor Kocher Institut, Berne, both of Switzerland

[21] Appl. No.: 471,817

[22] Filed: Jun. 6, 1995

Related U.S. Application Data

[63] Continuation of Ser. No. 141,890, Oct. 22, 1993, abandoned, which is a continuation of Ser. No. 947,225, Sep. 18, 1992, abandoned, which is a continuation of Ser. No. 572,966, Aug. 8, 1990, abandoned.

[30] Foreign Application Priority Data

Dec. 8, 1988 [GB] United Kingdom .................. 8828728
Apr. 27, 1989 [GB] United Kingdom .................. 8909681

[51] Int. Cl.$^6$ ......................... C07K 14/52; A61K 38/19
[52] U.S. Cl. ................ 424/85.1; 424/184.1; 424/198.1; 514/2; 514/8; 514/12; 514/885; 530/324
[58] Field of Search ..................... 530/300, 324; 514/2, 8, 12, 885; 424/85.1, 184.1, 198.1

[56] References Cited

U.S. PATENT DOCUMENTS 4,897,348  1/1990  Johnson et al. ........................ 435/69.1
5,026,639  6/1991  Johnson ................................ 435/69.1

FOREIGN PATENT DOCUMENTS

89/04325  5/1989  WIPO .

OTHER PUBLICATIONS

Ngo et al. (1994) in *The Protein Folding Problem & Tertirary Structure Prediction*, Meiz et al. (ed.), Birkhauser, Boston, MA pp. 492–495.
Begg et al., Biochemistry 17, 1739–1744 (1978).
Car et al., Biochem. J. 275, 581–584 (1991).
Castor et al., Proc. Natl. Acad. Sci. USA 80, 765–769 (1983).
Ferrante et al., J. Chromatogr. 440, 105–118 (1988).
Gregory et al., Biochem. Biophys. Res. Comm. 151, 883–890 (1988).
Jose et al., Biochem. J. 278, 493–497 (1991).
Lindley et al., Proc. Natl. Acad. Sci. USA 85, 9199–9203 (1988).
Matsuoka et al., Proc. Natl. Acad. Sci. USA 86, 4416–4420 (1989).

(List continued on next page.)

*Primary Examiner*—John Ulm
*Assistant Examiner*—Prema Mertz
*Attorney, Agent, or Firm*—Melvyn M. Kassenoff

[57] ABSTRACT

Peptides having the amino acid sequence

```
  1                     5                    10
X—Ala—Glu—Leu—Arg—Cys—Met—Cys—Ile—Lys—Thr—

11                    15                    20
Thr—Ser—Gly—Ile—His—Pro—Lys—Asn—Ile—Gln—

21                    25                    30
Ser—Leu—Glu—Val—Ile—Gly—Lys—Gly—Thr—His—

31                    35                    40
Cys—Asn—Gln—Val—Glu—Val—Ile—Ala—Thr—Leu—

41                    45                    50
Lys—Asp—Gly—Arg—Lys—Ile—Cys—Leu—Asp—Pro—

51                    55                    60
Asp—Ala—Pro—Arg—Ile—Lys—Lys—Ile—Val—Gln—

61                    65                    70
Lys—Lys—Leu—Ala—Gly—Asp—Glu—Ser—Ala—Asp,
``` wherein X is H, Asp-Leu-Tyr-, Ser-Asp-Leu-Tyr- or Asp-Ser-Asp-Leu-Tyr-. The peptide wherein X is H is human neutrophil-activating peptide-2 (hNAP-2) and those wherein X is other than H are natural variants thereof. The peptides have neutrophil-stimulating activity, are structurally related to NAF/NAP-1, β-thromboglobulin, PBP and CTAP-III and may be isolated from leukocytes and platelets and synthesized by standard peptide synthesis processes and recombinant DNA techniques.

10 Claims, 7 Drawing Sheets

OTHER PUBLICATIONS

Mullenbach et al., J. Biol. Chem. 261, 719–722 (1986).
Pencev et al., Oncogene Res. 3, 333–342 (1988).
Schroder et al., J. Immunol. 139, 3474–3483 (1987).
Schroder et al., J. Immunol. 140, 3534–3540 (1988).
Schroder et al., J. Exp. Med. 171, 1091–1100 (1990).
Schroder et al., Biochem. Biophys. Res. Comm. 172, 898–904 (1990).
Tanaka et al., FEBS Lett. 236, 467–470 (1988).
Walz et al., Biochem. Biophys. Res. Comm. 159, 969–975 (1989).
Walz et al., J. Exp. Med. 170, 1745–1750 (1989).
Walz et al., J. Exp. Med. 171, 449–454 (1990).
Wenger et al., Blood 73, 1498–1503 (1989).
Yoshimura et al., J. Immunol. 139, 788–793 (1987).

FIG. 2

```
1                 5                      10
Ala-Glu-Leu-Arg-Cys-Met-Cys-Ile-Lys-Thr- 11                15                     20
Thr-Ser-Gly-Ile-His-Pro-Lys-Asn-Ile-Gln-
```

FIG. 4

```
1                  5                      10
Ala-Glu-Leu-Arg-Cys-Met-Cys-Ile-Lys-Thr- 11                 15                     20
Thr-Ser-Gly-Ile-His-Pro-Lys-Asn-Ile-Gln- 21                 25                     30
Ser-Leu-Glu-Val-Ile-Gly-Lys-Gly-Thr-His- 31                 35                     40
Cys-Asn-Gln-Val-Glu-Val-Ile-Ala-Thr-Leu- 41                 45                     50
Lys-Asp-Gly-Arg-Lys-Ile-Cys-Leu-Asp-Pro- 51                 55                     60
Asp-Ala-Pro-Arg-Ile-Lys-Lys-Ile-Val-Gln- 61                 65                     70
Lys-Lys-Leu-Ala-Gly-Asp-Glu-Ser-Ala-Asp
```

FIG. 5

```
-66                                                                    -1
λC1                                                              λC2
    GGGCAACTCACCCTCACTCAGAGGTCTTCTGGTTCTGGAAACAACTCTAGCTCAGCCTTCTCCACC 1                                                                      54
ATG AGC CTC AGA CTT GAT ACC ACC CCT TCC TGT AAC AGT GCG AGA CCA CTT CAT
MET Ser Leu Arg Leu Asp Thr Thr Pro Ser Cys Asn Ser Ala Arg Pro Leu His 55                                                                    108
GCC TTG CAG GTG CTG CTG CTT CTG TCA TTG CTG CTG ACT GCT CTG GCT TCC TCC
Ala Leu Gln Val Leu Leu Leu Leu Ser Leu Leu Leu Thr Ala Leu Ala Ser Ser
                                                              PBP
                                                                  →162
109                  130             142
ACC AAA GGA CAA ACT AAG AGA AAC TTG GCG AAA GGC AAA GAG GAA AGT CTA GAC
Thr Lys Gly Gln Thr Lys Arg Asn Leu Ala Lys Gly Lys Glu Glu Ser Leu Asp
                        CTAP-III       βTG
                           →              →
163                                                                   216
                175
AGT GAC TTG TAT GCT GAA CTC CGC TGC ATG TGT ATA AAG ACA ACC TCT GGA ATT
Ser Asp Leu Tyr Ala Glu Leu Arg Cys Met Cys Ile Lys Thr Thr Ser Gly Ile
                NAP-2              *   ■
                   →

217                                                                   270
CAT CCC AAA AAC ATC CAA AGT TTG GAA GTG ATC GGG AAA GGA ACC CAT TGC AAC
His Pro Lys Asn Ile Gln Ser Leu Glu Val Ile Gly Lys Gly Thr His Cys Asn
                                                                    *
271                                                                   324
CAA GTC GAA GTG ATA GCC ACA CTG AAG GAT GGG AGG AAA ATC TGC CTG GAC CCA
Gln Val Glu Val Ile Ala Thr Leu Lys Asp Gly Arg Lys Ile Cys Leu Asp Pro
                                                         ■
325                                                                   378
GAT GCT CCC AGA ATC AAG AAA ATT GTA CAG AAA AAA TTG GCA GGT GAT GAA TCT
Asp Ala Pro Arg Ile Lys Lys Ile Val Gln Lys Lys Leu Ala Gly Asp Glu Ser 379                                                                   447
GCT GAT TAATTTGTTCTGTTTCTGCCAAACTTCTTTAACTCCCAGGAAGGGTAGAATTTTGAAACCTTG
Ala Asp TER 448                                                                   518
AT TCTAGAGTTCTCATTTATTCAGGATACCTATTCTTACTGTATTAAAATTTGGATATGTGTTTCATTC 519                                                                   589
TGTCTCAAAAATCACATTTTATTCTGAGAAGGTTGGTTAAAAGATGGCAGAAAGAAGATGAAAATAAATAA 590            624
GCCTGGTTTCAACCCTCTAAAAAAAAAAAAAAAAA
```

NEUTROPHIL-ACTIVATING PEPTIDE-2

This is a continuation of application Ser. No. 08/141,890, filed Oct. 22, 1993 and now abandoned, which is a continuation of application Ser. No. 07/947,225, filed Sep. 18, 1992 and now abandoned, which is a continuation of application Ser. No. 07/572,966, filed Aug. 8, 1990 and now abandoned, which is a 371 of International Application No. PCT/EP89/01389) filed Nov. 17, 1989.

The present invention is concerned with an immunomodulatory substance.

It is more particularly concerned with an immunostimulating factor which activates neutrophil leukocytes, especially human neutrophil leukocytes. It is hereinafter referred to as neutrophil-stimulating activity 1 (NSA-1) or, synonymously, neutrophil-activating peptide 2 (NAP-2).

BACKGROUND

The neutrophil leukocytes (neutrophils) are the most common leukocytes and account for about ⅔ of the white cells in human blood. They have one main function which is to protect the host organism against microbial infections. The neutrophils are mobile, responsive to chemotactic stimuli generated upon infection and able to move into infected tissues to kill the microorganisms. The killing depends on the ability of the neutrophils to engulf the microorganisms and to release oxygen radicals and microbiocidal enzymes. The release of such products depends on activation of the neutrophils.

A few proteins having such activity are known, such as neutrophil-activating factor (NAF) (P. Peveri et al., *J. Exp. Med.* 167 [1988] 1547), also termed neutrophil-activating peptide 1 (NAP-1).

SUMMARY OF THE INVENTION

It has now been found that neutrophil-stimulating activity is produced by stimulated leukocytes in culture and can be obtained from the culture fluid. The neutrophil-stimulating activity is referred to herein as NSA-1 or, synonymously, neutrophil-activating peptide-2 (NAP-2).

It has also been found that NSA-1/NAP-2 is structurally very similar to β-thromboglobulin (β-TG), connective tissue activating peptide III (CTAP-III) and platelet basic protein (PBP).

It is an object of the invention to provide NSA-1/NAP-2 or a functional variant, fragment or derivative thereof still having this biological activity, e.g. a mutein, in a degree of purity sufficient to allow its further characterization and preparation by, e.g., recombinant DNA techniques, and its pharmaceutical use.

The invention further provides a process for the preparation of NSA-1/NAP-2 from, e.g., human blood leukocytes and/or platelets.

It further provides for the use of NSA-1/NAP-2 in activating neutrophil leukocytes and thus enhancing resistance to infections.

It further provides a process for preparing NSA-1/NAP-2 or a functional variant, fragment or derivative thereof, or of a biologically active structural relative thereof such as β-TG, CTAP-III or PBP by recombinant DNA techniques which comprises cloning a corresponding gene including a natural leader sequence, e.g. a natural leader sequence endogenous to human platelets, expressing it in a suitable host and appropriately recovering the peptide product, if indicated using an appropriate protease.

ABBREVIATIONS

BSA bovine serum albumin
CTAP-III connective tissue-activating peptide III
SDSI sodium dodecyl sulfate
DTT dithiothreitol
fMLP N-formyl-L-methionyl-L-leucyl-L-phenylalanine
LPS lipopolysaccharide from *E.coli* O55:D5
MEM Eagle's minimal essential medium (Seromed GmbH, Munich, FRG), supplemented with 25 µg/ml neomycin, buffered to pH 7.4 with 25 mM NaHCO$_3$ and 20 mM HEPES
MEM-PPL contains in addition 1% pasteurized plasma protein solution (5% PPL-SRK, Swiss Red Cross Laboratory, Bern, Switzerland) and 100 IU/ml penicillin and streptomycin (Gibco AG, Basel, Switzerland)
MoAbs monoclonal antibodies
MRNA messenger RNA
NAF neutrophil-activating factor (=NAP-1)
NAP-1 neutrophil-activating peptide 1 (=NAF)
NAP-2 neutrophil-activating peptide 2 (=NSA-1)
NEM N-ethylmaleimide
NSA-1 neutrophil-stimulating activity 1 (=NAP-2)
PBP platelet basic protein
PBS phosphate-buffered saline without Ca$^{++}$ and Mg$^{++}$
PBS-BSA PBS supplemented with 0.9 mM CaCl$_2$, 0.49 mM MgCl$_2$ and 2.5 mg/ml BSA
PRP platelet-rich plasma
PHA-P Phytohemagglutinin (Difco Laboratories, Detroit, Mich., USA)
PMN polymorphonuclear cells-neutrophils
PMSF Phenylmethanesulfonyl fluoride
SDS-PAGE sodium dodecyl sulfate polyacrylamide gel electrophoresis
SSPE 180 mM NaCl; 10 mM NaH$_2$PO$_4$; 1 mM EDTA; pH 7.4
β-TG β-thromboglobulin

DETAILED DESCRIPTION

NSA-1/NAP-2 is characterized biologically by its neutrophil-activating properties, in particular the induction of granule enzyme release. In molecular terms NSA-1/NAP-2 is characterized by a molecular weight of approximately 7500 and a calculated isoelectric point of approximately 8.7.

It is produced from, e.g., human blood leukocytes and/or platelets by a process comprising purification from culture fluids of stimulated blood leukocytes and/or platelets by phosphocellulose chromatography and reversed-phase chromatography.

NSA-1/NAP-2 from species other than human may be produced in similar manner from corresponding blood leukocytes and/or platelets.

Stimulation may be effected with any known agent such as LPS and PHA-P.

Phosphocellulose chromatography may, e.g., be effected on a phosphocellulose column equilibrated with a potassium phosphate/NaCl/EDTA/glycerol buffer at approximately neutral pH, e.g. pH 7.2, and subsequent elution in, e.g., a linear NaCl concentration gradient in the same buffer.

Reversed-phase chromatography preferably follows phosphocellulose chromatography and preferably is effected first on a preparative reversed-phase C4 column eluted with, e.g., a 0 to 80% gradient of acetonitrile in 0.1% trifluoroacetic acid; then on a CN-propyl column eluted with, e.g., a gradient of 0–80% acetonitrile in 0.1% trifluoroacetic acid;

and thereafter the active fractions are rerun on an analytical reversed-phase C4 column under conditions similar to those used for the CN-propyl chromatography.

The course of the purification may be seen from FIGS. 1a, 1b and 1c.

The course of the purification is followed by analysis for neutrophil-stimulating activity, e.g., as the capacity to induce release of elastase from human neutrophils pretreated with cytochalasin B (B. Dewald and M. Baggiolini, *Biochem. Pharmacol.* 36 [1987] 2505–2510).

The NSA-1/NAP-2 is found to have an apparent molecular weight of approximately 6500 upon 20% urea—SDS polyacrylamide gel electrophoresis. The apparent isoelectric point is about 8.3.

Amino acid sequence analysis shows (FIG. 2) that the first 20 N-terminal amino acids correspond exactly to a common portion of the sequence of platelet basic protein (PBP) and its structural derivatives CTAP-III (C. W. Castor et al., *PNAS* 80 [1983] 765–769) and β-thromboglobulin (G. S. Begg et al., *Biochemistry* 17 [1978] 1739–1744). The amino-terminus of NSA-1/NAP-2 corresponds to amino acid 16 of CTAP-III and amino acid 12 of β-TG. Digestion with carboxypeptidase Y shows that the C-terminal amino acid sequences are identical (-Glu-Ser-Ala-Asp). NSA-1/NAP-2 aligns completely to the sequence of β-TG and consists of 70 amino acids with a calculated molecular weight of 7628 and a calculated isoelectric point of 8.7. The full 70 amino acid sequence is shown in FIG. 4. The overall homology between NSA-1/NAP-2 and NAF/NAP-1 is 46%. The NSA-1/NAP-2 sequence does not contain any apparent sites for N-glycosylation. There is a potential site for phosphorylation by protein kinase C (Thr) at position 39 and a possible amidation site (Asp) at position 42.

NSA-1/NAP-2 can thus be viewed as being a fragment of β-TG.

The sequence of NSA-1/NAP-2 can be aligned to that of NAF/NAP-1 on the basis of the two first cysteine residues (Cys 5 and Cys 7 for NSA-1/NAP-2 and Cys 7 and Cys 9 for NAF/NAP-1). When aligned in this way, about one half of the first 20 amino acids of NSA-1(NAP-2 and NAF/NAP-1 are identical. The two factors are thus related not only functionally but also to a certain degree structurally.

The availability of the amino acid sequence of NSA-1/NAP-2 allows its preparation by further processes in addition to the isolation from a natural source described above. Thus, since the peptide includes only 70 amino acids, total synthesis is possible in conventional manner, e.g., using the Merrifield solid phase method and having due regard to the presence of two disulfide bonds.

Further production processes include recombinant DNA techniques, e.g., by cloning and expression of a corresponding synthetic gene, optionally after codon optimization. The chemical synthesis and expression in yeast of a gene encoding CTAP-III has been described (G. T. Mullenbach et al., *J. Biol. Chem.* 261 [1986] 719) and is thus also applicable to the production of related peptides such as NSA-1/NAP-2. However, only part of the CTAP-III produced had biological activity. It seems likely that misfolding and incorrect disulfide-bond formation were major problems. No DNA coding for a leader sequence was incorporated in the synthetic gene since no such leader sequence was yet known for this class of compounds.

A further method of production by recombinant DNA techniques is the cloning and expression of a gene including a natural leader sequence, e.g., a natural leader sequence endogenous to human platelets, e.g., by cloning and expression of a cDNA selected from an appropriate expression library and coding for NSA-1/NAP-2 or a larger peptide encompassing NSA-1/NAP-2 such as β-TG, CTAP-III or PBP and recovery of NSA-1/NAP-2 in conventional manner from the expression product. Such a leader sequence is, e.g., the first 34 amino acids in the sequence of FIG. 5, or a functional fragment or derivative thereof. Example 7 describes the cloning of a cDNA coding for CTAP-III from a human platelet-derived λgt11 expression library. Recovery of the desired peptide product from a larger parent peptide may, e.g., be effected by appropriately truncating the larger peptide in conventional manner with a protease such as a serine protease.

Appropriate proteases may, e.g., be isolated in conventional manner from purified monocytes. They are highly sensitive to PMSF, moderately sensitive to leupeptin and insensitive to EDTA.

Alternatively, the leader sequence may be directly attached to the gene coding for the desired peptide.

Preparation via cloning of a gene including a natural leader sequence results in peptide products having the proper folding for full biological activity, e.g., for targeting to the α-granule, when expressed in mammalian cells.

Functional fragments or derivatives, e.g., muteins, of NSA-1/NAP-2 may be prepared according to methods known in the art.

Three variants of NSA-1/NAP-2 with somewhat reduced biological activity have also been found, having the 70 amino acid sequence shown in FIG. 4 but elongated at the N-terminus by the 3, 4 and, respectively, 5 corresponding amino acids of CTAP-III (see FIG. 5). They thus have the sequence of FIG. 4 preceded by, respectively:

Asp-Leu-Tyr-,

Ser-Asp-Leu-Tyr- and

Asp-Ser-Asp-Leu-Tyr and are of 73, 74 and, respectively, 75 amino acids in length.

They can be produced as described above for the preparation of NAP-2 from stimulated blood leukocytes and/or platelets: upon stimulation with LPS in the presence of monocyte culture supernatant, in addition to NAP-2 a smaller intermediate peak containing the 73–75 residue variants of NAP-2 is obtained. This additional peak is made up to 65, 20 and 15 percent by the 74, 75 and 73 residue form, respectively.

NSA-1/NAP-2 and functional variants, fragments and derivatives thereof possess biological activity making them indicated for use as pharmaceuticals.

For example, they elicit neutrophil infiltration in rats in dosage of from about 1 µg/kg to about 100 µg/kg animal body weight.

NSA-1/NAP-2 and functional variants, fragments and derivatives thereof are thus indicated for use in the treatment of conditions which are accompanied or caused, locally or systemically, by a modification of the number or activation state of the PMN (polymorphonuclear cells—neutrophils). They extensively modify these PMN parameters and are therefore indicated for use in the treatment of conditions in which an increase of the number or enhancement of the activation state of the PMN leads to clinical improvement, e.g., in bacterial, mycoplasma, yeast and fungal, and in viral infections. Furthermore, they are indicated for use in inflammatory illnesses such as psoriasis, arthritic conditions and asthma, or in conditions of abnormally low neutrophil count and/or generalized low neutrophil level, and in the preparation of antagonists, e.g., monoclonal antibodies, for use in these indications.

Since, as NAP-1, they have been shown to be also chemotactic for T-lymphocytes, they are also indicated for use in certain immunodeficient states.

For these indications the appropriate dosage will, of course, vary depending upon, for example, the host, the mode of administration and the nature and severity of the condition to be treated. However, in general, satisfactory results are indicated to be obtained systemically at daily dosages of from about 1 mg/kg to about 100 mg/kg animal body weight. For the larger subject an indicated daily dosage is in the range of from about 0.1 mg to about 100 mg, preferably from about 0.1 mg to about 10 mg, conveniently administered, for example, in divided doses up to four times a day.

Pharmaceutical compositions comprising the compound in association with at least one pharmaceutically acceptable carrier or diluent can be manufactured in conventional manner by mixing with a pharmaceutically acceptable carrier or diluent. Unit dosage forms contain, for example, from about 0.025 mg to about 50 mg of the compound.

While functionally largely similar to NAP-1, NSA-1/NAP-2 can probably only be generated in vivo when PBP and/or CTAP-III are liberated from platelets, while the production of NAF/NAP-1 by mononuclear phagocytes and a wide variety of tissue cells is induced by inflammatory cytokines like tumor necrosis factor and interleukin-1. The two peptides must, therefore, be expected to arise in dissimilar physiological situations and at different sites. Being platelet derived, NAP-2 is produced mainly intravascularly, where platelet activation and aggregation occurs, e.g., in thrombi and atherosclerotic lesions, while NAF/NAP-1 almost invariably forms in the tissues.

NSA-1/NAP-2 and its variants are not found in platelets or other components of the mononuclear cell cultures and appear to be formed following release. They exhibit the typical properties of chemotactic receptor agonists and induce cytosolic free calcium changes, chemotaxis and exocytosis in the same molar range as NAF/NAP-1, while PBP, CTAP-III and PF-4 have little if any activity at 100 to 10000 times higher concentrations. They are expected to be as effective as NAF/NAP-1 and C5a in the recruitment of neutrophils and to have a role in thrombosis, where they could attract neutrophils involved in the recanalization of obstructed vessels.

BRIEF DESCRIPTION OF THE DRAWINGS

FIG. 1b: Reversed-phase high pressure liquid chromatography of NSA-1/NAP-2 on a CN-propyl column. Details as in FIG. 1a.

FIG. 1c: Reversed-phase high pressure liquid chromatography of NSA-1/NAP-2 on a C4 column. Details as in FIG. 1a.

FIG. 2: Amino-terminal sequence of NSA-1/NAP-2. The first 20 residues are shown. They correspond to part of the sequence of β-thromboglobulin.

FIG. 4: Amino acid sequence of NSA-1/NAP-2.

FIG. 5: cDNA sequence and deduced amino acid sequence of the precursor of PBP (starts with nucleotide 103), CTAP-III (starts with nucleotide 130), β-TG (starts with nucleotide 142) and NSA-1/NAP-2 (starts with nucleotide 175). The two internal disulfide bonds are identified with asterisks and squares respectively. The putative polyadenylation signal is underlined (nucleotides 581–586). The EcoRI recognition site is overlined.

EXAMPLES

Figure 1A:
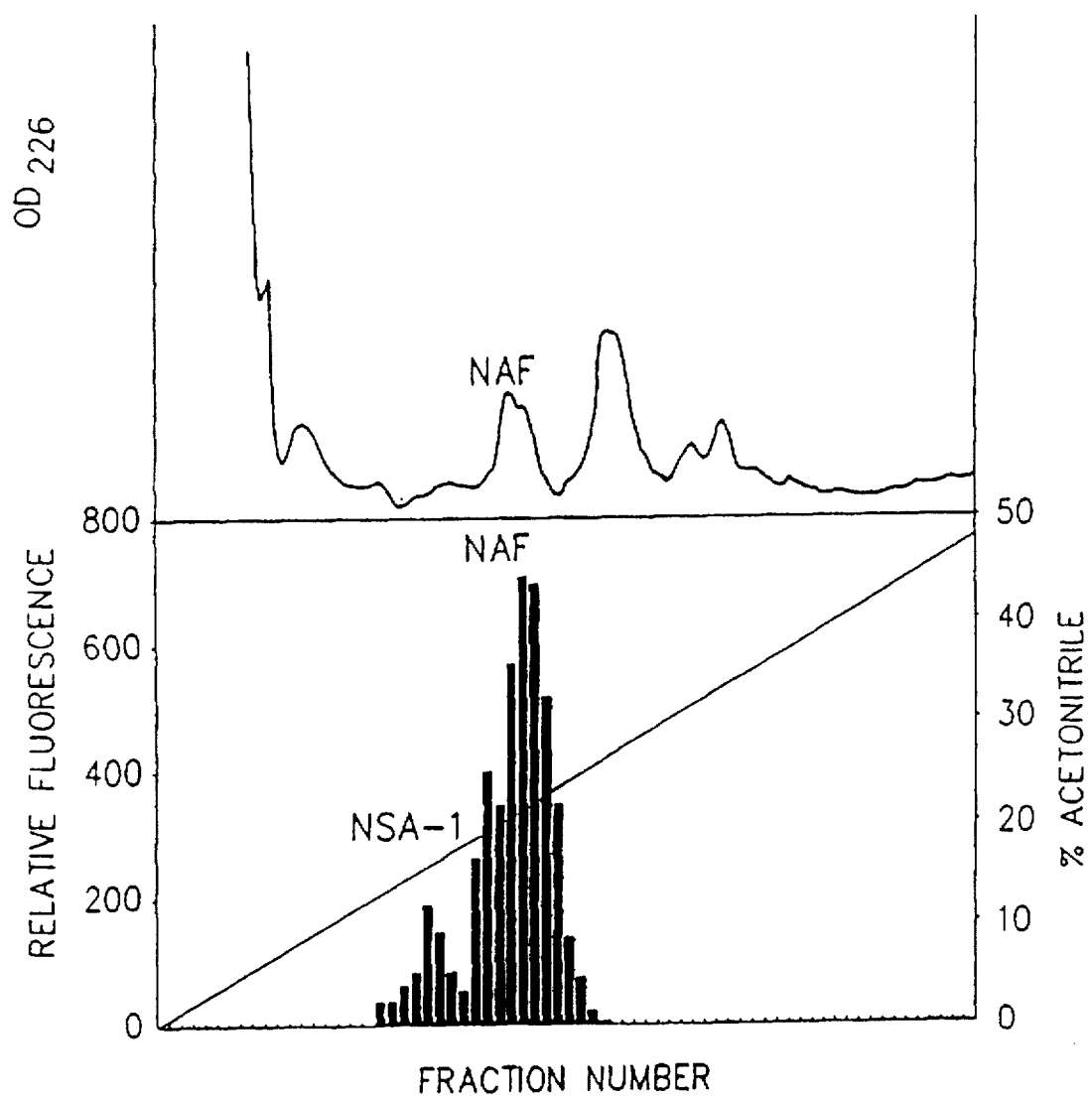
FIG. 1a: Preparative reversed-phase high pressure liquid chromatography of NSA-1 on a C4 column. Upper graph: protein distribution, OD at 226 nm; lower graph: NSA-1 activity, relative release of elastase from human neutrophils. Two peaks are evident: a small one corresponding to NSA-1/NAP-2 and a larger one corresponding to NAF/NAP-1.

The following Examples illustrate the invention.

PART 1

PRODUCTION OF NSA-1/NAP-2 FROM HUMAN BLOOD, PURIFICATION AND CHARACTERIZATION

Example 1

Production of NSA-1/NAP-2 by human blood leukocytes and/or platelets stimulated with LPS Anticoagulated donor blood, obtained from the Swiss Red Cross Laboratory and stored for up to 20 hours at 4°–10° C., was used. Mononuclear cells (consisting of monocytes and lymphocytes in a ratio of approximately 1:5) were isolated from single buffy coats on Ficoll-Hypaque gradients (A. Boyum, Scand. J. Immunol. 5 [1976] 9–15), and were washed in MEM. The washed cells from 6 buffy coats were resuspended in MEM-PPL ($5 \times 10^6$ cells/ml) and cultured for 20 hours in the presence of 1 µg/ml LPS in glass bottles equipped with a stirring device. At different times, aliquots of the culture media were sampled and the neutrophil-stimulating activity was determined as the capacity to induce release of elastase from human neutrophils pretreated with cytochalasin B (B. Dewald and M. Baggiolini, Biochem. Pharm. 36 [1987] 2505–2510). This test detects NSA-1 as well as NAF, a previously described neutrophil-activating factor (P. Peveri et al., J. Exp. Med. 167 [1988] 1547–1559). Neutrophil-stimulating activity increased with time and levelled off after 24 to 48 hours.

Example 2

Production of NSA-1/NAP-2 by human blood leukocytes and/or platelets stimulated with PHA-P Anticoagulated donor blood, obtained from the Swiss Red Cross Laboratory and stored for up to 20 hours at 4°–10° C., was used. Mononuclear cells (consisting of monocytes and lymphocytes in a ratio of approximately 1:5) were isolated from single buffy coats on Ficoll-Hypaque gradients (Boyum, 1976) and were washed in MEM. The washed cells from 6 buffy coats were resuspended in MEM-PPL ($5 \times 10^6$ cells/ml) and cultured for 20 hours in the presence of 5 µl/ml PHA-P in glass bottles equipped with a stirring device. At different times, aliquots of the culture media were sampled and the neutrophil-stimulating activity was determined as the capacity to induce release of elastase from human neutrophils pretreated with cytochalasin B. Neutrophil-stimulating activity increased with time and levelled off after 24 to 48 hours.

Example 3

Purification of NSA-1/NAP-2 from the culture fluids of stimulated human blood leukocytes and/or platelets stimulated with LPS a) Phosphocellulose chromatography Portions of 700 ml of cell-free culture fluids of human leukocytes stimulated as described in Example 1 were

7 directly loaded onto a 15 ml phosphocellulose column (Whatman P11) equilibrated with buffer A (20 mM potassium phosphate buffer, pH 7.2, containing 20 mM NaCl, 1 mM EDTA and 5% glycerol). The column was washed with the same buffer and then eluted (24 ml/hour) with 120 ml of a linear NaCl concentration gradient (0.02 to 1.5M) in buffer A. Fractions were analyzed for neutrophil-stimulating activity.

b) Reversed-phase chromatography

Active fractions obtained from the phosphocellulose chromatography separation were pooled and further purified by 4 repeated runs on a wide-pore preparative reversed-phase C4 column (10×250 mm, 7 µm, Macherey-Nagel, Dueren, FRG). The column was eluted at 2 ml/min with a gradient of 0 to 80% acetonitrile in 0.1% trifluoroacetic acid with an increment of 0.66% per min.

Figure 1B:
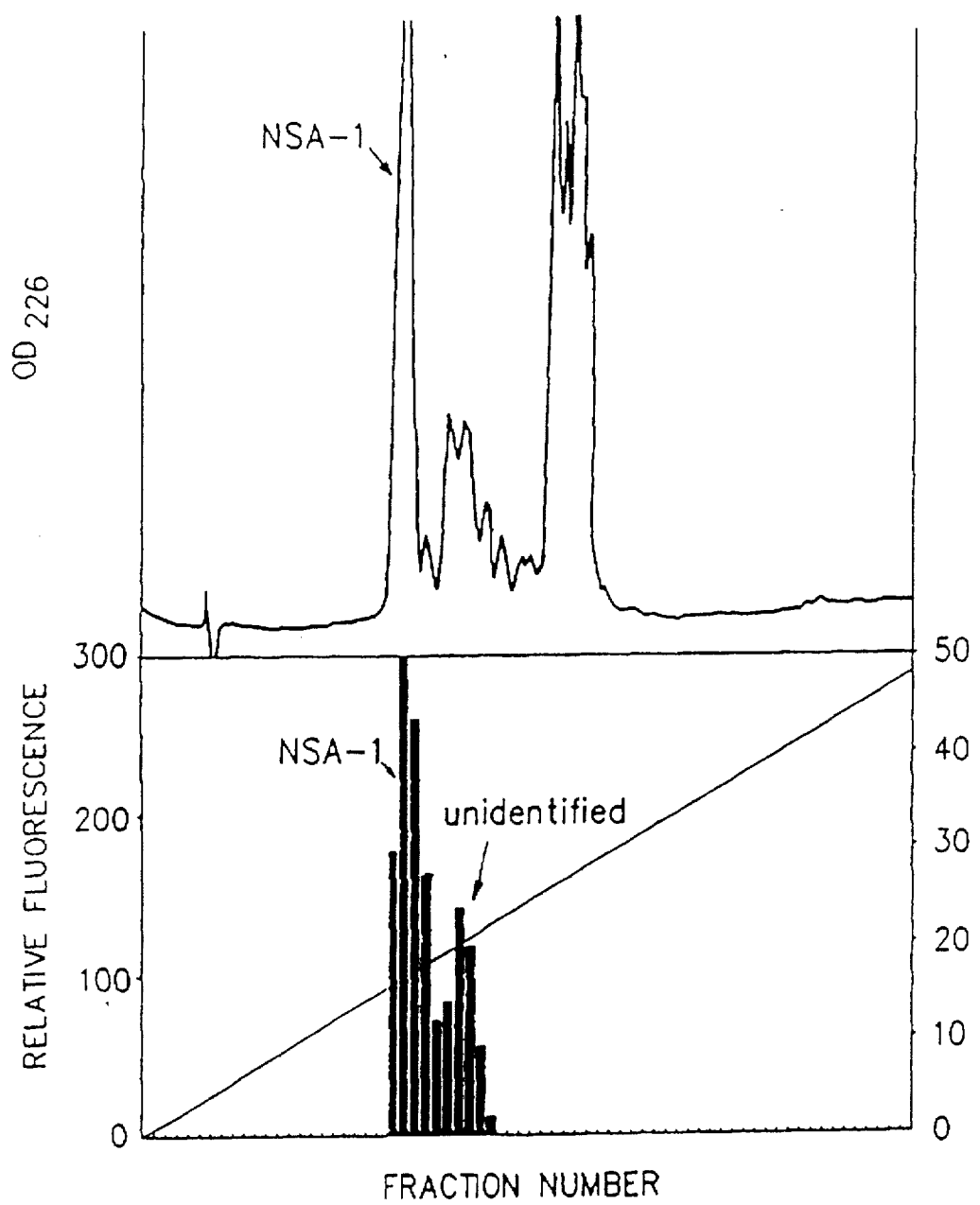
Figure 1C:
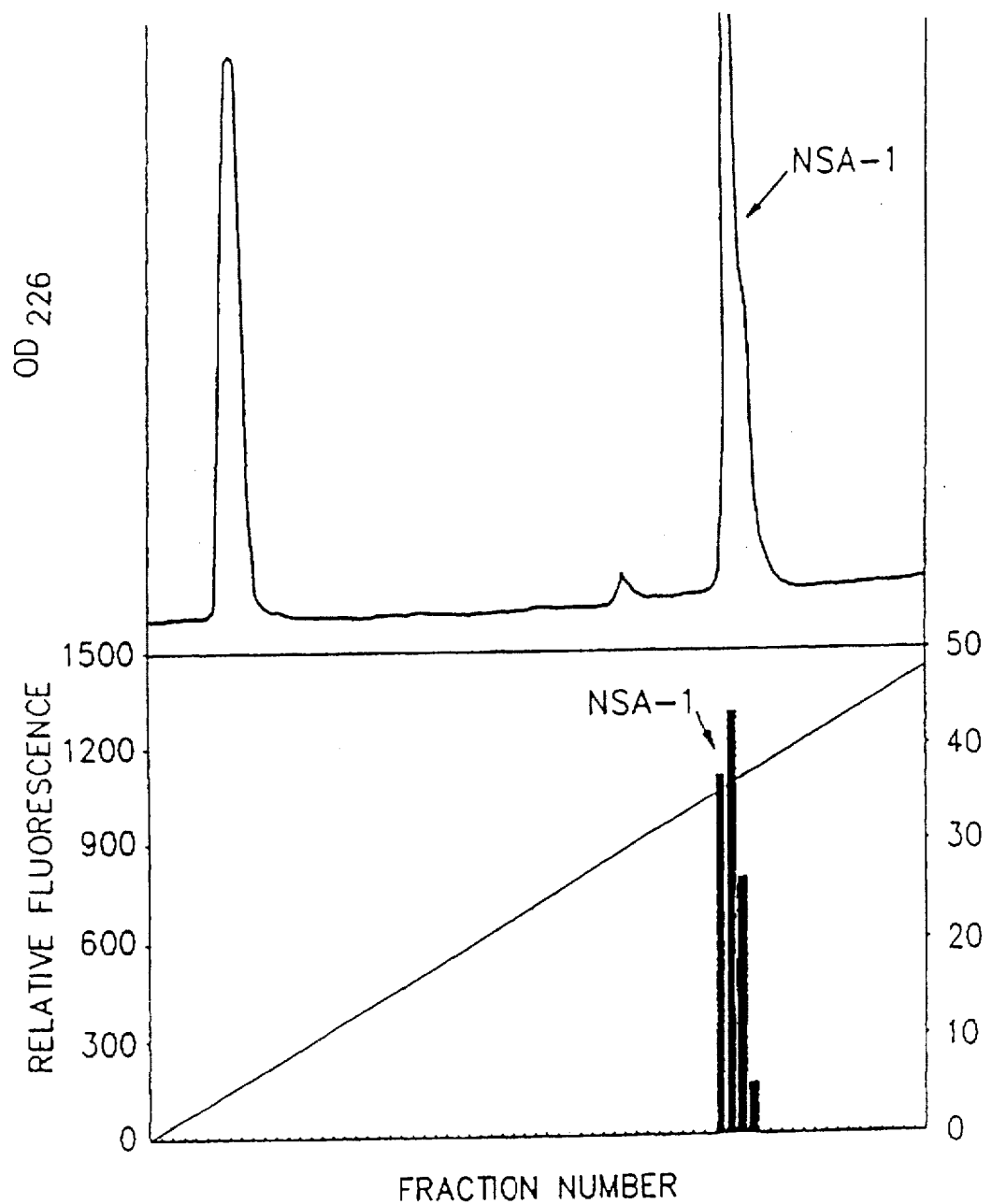

Active fractions with a retention time of 20–26 min were pooled, concentrated on a Speed Vac centrifuge and loaded onto an analytical reversed-phase CN-propyl column (4.6× 250 mm, 5 µm, wide-pore, Baker Research Products, Phillipsburg, N.J., USA). The column was eluted at 0.5 ml/min with a gradient of 0 to 80% acetonitrile in 0.1% trifluoroacetic acid with an increment of 0.66% per min. Active fractions with a retention time of 22–25 min were pooled, concentrated and rerun on an analytical reversed-phase C4-column (4.6×250 mm, 5 µm, wide-pore, Baker Research Products) under the conditions described for the CN-propyl column. Active fractions with a retention time of 42.5 min were dried in a Speed Vac centrifuge, resuspended in sterile water and then used for gas-phase sequence analysis and for biological testing. FIG. 1 shows the separation of NSA-1/NAP-2 from NAF/NAP-1 and the fractions used for amino acid sequence analysis.

Example 4

Gel electrophoresis of purified NSA-1/NAP-2

Purified NSA-1/NAP-2 was analyzed on a 20% urea-SDS polyacrylamide gel according to B. Kadenbach et al., *Analyt. Biochem.* 129 [1983] 517–521). A single band with an apparent molecular weight of 6500 was obtained upon visualization by silver staining. NAP-2 migrated slightly faster than NAF/NAP-1.

Example 5

Amino acid sequence analysis of NSA-1/NAP-2

Amino acid sequence analysis was performed by automated phenyl isothiocyanate degradation using an Applied Biosystems gas phase sequencer Model 477 A. Samples of NSA-1/NAP-2 (500 pMol) were applied directly or after chemical modification. Reduction and alkylation were performed as follows: 1 nMol of NSA-1/NAP-2 was diluted in 150 µl of 6M guanidinium hydrochloride, 2 mM EDTA, 0.2M Tris-HCl, pH 8.3, then 225 nl of tributylphosphine in 15 µl acetonitrile were added and the solution incubated at room temperature. After 60 min 160 nl of 4-vinylpyridine in 10 µl acetonitrile were added. After 30 min an equal amount of tributylphosphine and vinylpyridine was added, and the reaction was continued for another 40 min under nitrogen. The solution was acidified with trifluoroacetic acid to pH 2.0 and desalted by reversed-phase HPLC in 0.1% trifluoroacetic acid with an acetonitrile gradient.

The carboxy-terminus was determined with 0.5 nmol of NAP-2 and 0.4 µg of carboxypeptidase P or carboxypeptidase Y (sequencing grade, Boehringer).

FIG. 2 shows the analysis of the first 20 aminoterminal amino acids.

8

Example 6

Neutrophil-activating effect of NSA-1/NAP-2

Neutrophils were isolated from human blood, suspended in PBS/BSA and then used to assess the capacity of NSA-1/NAP-2 to induce elastase release using the microtiter plate assay method of Dewald and Baggiolini (1987). NSA-1/NAP-2 induced the selective release of elastase in a concentration-dependent manner. The concentration dependance was similar to that observed with NAF/NAP-1 and the potency was about half of that of NAF and about one third of that of fMLP.

Figure 3:
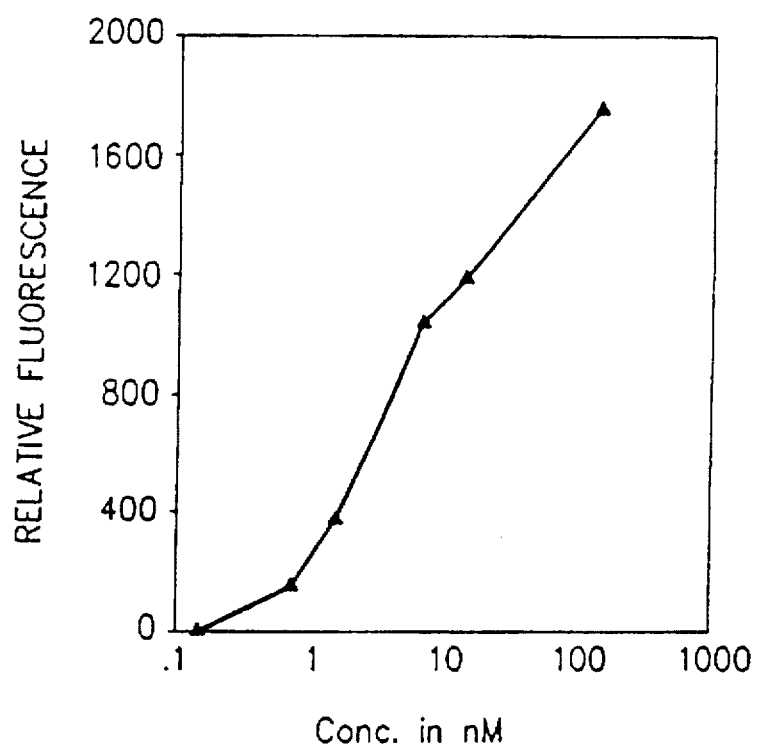
FIG. 3: NSA-1/NAP-2-induced exocytosis in cytochalasine B—treated human neutrophils. Concentration dependance.

FIG. 3 shows the concentration-dependent activity of NSA-1/NAP-2.

PART II

CLONING OF cDNA CODING FOR CTAP-III FROM A HUMAN PLATELET-DERIVED λgt11 EXPRESSION LIBRARY

Example 7 a) Isolation and washing of platelets

Platelets were isolated from citrate-treated blood by centrifugation at 160 g for ten minutes to give platelet-rich plasma (PRP) and by a further centrifugation step at 1100 g for ten minutes to give a platelet pellet. The platelets were then washed twice with 30 mmol/l glucose, 120 mmol/l NaCl, 129 mmol/l sodium citrate, 10 mmol/l EDTA pH 6.5, and once with 10 mmol/l Tris/HCl, 154 mmol/l NaCl, 10 mmol/l EDTA pH 7.4.

b) Human megakaryocytes

These were isolated from the peripheral blood of a patient with megakaryoblastic leukemia by Ficoll-metrizoate gradient density centrifugation. The megakaryoblastic phenotype of these leukemic cells is based on their reactivity with monoclonal antibodies (MoAbs) to platelet GPIIb, the GPIIb/GPIIIa complex and (vWF) von Willebrand factor. A cDNA probe for platelet GPIb also gave a positive signal with a messenger RNA (mRNA) of 2.4 kb (same size as in platelets) in Northern blotting with mRNA from these cells.

c) Preparation of antibodies

Washed platelets were solubilized in 1% Triton X-114 in the presence of N-ethylmaleimide (NEM) and phenylmethanesulfonyl fluoride (PMSF, dissolved in methanol) at a final concentration of 2 mmol/l each and phase partition was carried out as described in *Biochim. Biophys. Acta* 778 (1984) 463. The aqueous phase was used for AcA-34 Ultrogel (LKB) exclusion chromatography in 0.1% sodium dodecyl sulfate (SDS), 0.1 mol/l $NH_4HCO_3$, pH 7.4. A fraction containing proteins in the 8- to 9- kD range, as estimated by sodium dodecyl sulfate-polyacrylamide gel electrophoresis (SDS-PAGE) was used for immunization of rabbits.

d) Immunoblotting

Degranulation products were obtained from the supernatant of washed platelets stimulated with thrombin (2 U/4× $10^9$/ml, five minutes, 37° C.) and treated with 2 mmol/l PMSF and 2 mmol/l NEM. They were solubilized in 1% SDS, reduced with 0.1% dithiothreitol (DTT), and separated by 20% SDS-PAGE followed by electrophoretic transfer to nitrocellulose (BA 85, Schleicher & Schuell, Feldbach, Switzerland) with a semidry electroblotter at 150 mA for 90 minutes. After incubation with an anti-CTAP-III rabbit polyclonal antiserum, a goat antirabbit second antibody coupled to alkaline phosphatase (Bio-Rad Laboratories, Glattbrugg, Switzerland) was used for staining with the substrates nitro blue tetrazolium and 5-bromo-4-chloro-3-indolyl phosphate.

e) Construction of the cDNA expression library

Total RNA of platelets from 180 l blood was prepared using the guanidine hydrochloride procedure. PolyA MRNA was isolated by oligo(dT) cellulose (Pharmacia, Uppsala, Sweden) affinity chromatography. First strand was synthesized using oligo(dT) primers (Pharmacia P-L Biochemicals) and reverse transcriptase (Bethesda Research Laboratories, Gibco, Basel, Switzerland). The second strand was prepared with RNase H (New England Biolabs, Schwalbach bei Frankfurt, FRG) and Escherichia coli DNA polymerase I (Boehringer Mannheim, Rotkreuz, Switzerland). After producing blunt ends with T4 DNA polymerase and Klenow enzyme, EcoRI methylation, and ligation to EcoRI linkers, the resulting cDNA was packaged in λgt11 packaging extract (Gigapack Gold, Stratagene, San Diego, Calif.) and amplified in E.coli y1088.

f) Library screening and characterization of positive clones

The platelet λgt11 cDNA expression library was screened by standard method with the polyclonal rabbit antiserum. E.coli-specific antibodies were removed by immunoadsorption on nitrocellulose-bound lysate of E.coli BNN97. Positive recombinant phages were detected by the same second antibody and chromogenic substrates as for immunoblotting. After purification, λ-DNA was digested with EcoRI (Boehringer Mannheim) and the inserts isolated by 0.8% agarose gel electrophoresis and electroelution in a Bio-Trap (Schleicher & Schuell). The DNA was precipitated with ethanol and ligated to 5 ng EcoRI linearized M13 Bluescript (Stratagene) using T4 ligase (Bio-Lab) and transfected into E.coli JM 101. White colonies were tested for positive recombinant plasmids by the alkaline extraction procedure and single stranded cDNA templates were prepared by infection with M13K07 helper phage. The DNA sequence of both strands was determined by the dideoxy-chain termination method using the Sequenase Kit (United States Biochemical Corporation) and $^{35}$S a-labeled dATP (New England Nuclear, Du Pont).

g) Northern blot analysis

Following electrophoresis in a 1% agarose gel, mRNA was blotted onto Hybond N (Amersham) and was then hybridized with a sulfonylated cDNA probe at 68° C. for 18 hours in 4×SSPE, 0.1% $Na_4P_2O_7$, 0.2% SDS, 0.5 mg/ml heparin containing 100 µg/ml salmon sperm DNA. After washing twice for five minutes in 1×SSPE, 1% SDS, 0.1% $Na_4P_2O_7$ at room temperature and twice for 30 minutes in 0.2×SSPE, 0.1% SDS, 0.1% $Na_4P_2O_7$ at 68° C., the corresponding mRNA was detected by immunostaining with a murine monoclonal antibody (MoAB; Sigma, Deisenhofen, FRG) against sulfonylated DNA and a goat antimouse IgG second antibody conjugated to alkaline phosphatase. The substrates were the same as above.

h) Results

Polyclonal antibodies produced by immunization of rabbits with a gel filtration fraction containing platelet water-soluble proteins in the 8 to 9 kD range showed a high avidity and specificity on immunoblots and were used for screening a platelet-derived λgt11 cDNA expression library. Two positive clones, from 100 000 initially screened recombinant phages, were plaque purified, and the two internal EcoRI fragments were subcloned in M13 Bluescript®. Nucleotide sequences of both strands were determined by the dideoxy-chain termination method. A full-length cDNA clone (λCI) of 690 base pairs was obtained (FIG. 5) containing a 5' non-coding region of 66 base pairs, an open reading frame coding for a protein of 128 amino acid residues (13 894 da) and a 3' non-coding region containing the termination codon (TAA), the putative polyadenylation signal, and the polyA tail. A second clone (λC2), starting at the relative position -9, showed an identical nucleotide sequence.

The consensus sequence for initiation of translation in eukaryotic MRNA (5' CCACCAUGA 3') begins at nucleotide -5.

Northern blot hybridization of MRNA from a megakaryocytic leukemia cell line, megakaryocytes, and platelets but not from a hepatocyte control gave a positive signal at approximately 0.8 kb with the MRNA of the CTAP-III precursor, suggesting that the corresponding cDNA is full length. No signal was obtained with HEL mRNA, possibly due to lower sensitivity of the nonradioactive labeling method for the cDNA probe and/or the low CTAP-III-specific MRNA content of the HEL cell line used.

The deduced amino acid sequence (FIG. 5) is identical to the well-established sequence of human platelet CTAP-III. The amino terminus of CTAP-III is at amino acid position 44 of the translated sequence, and the beginning of its mitogenically inactive plasmin or trypsin degradation product β-thromboglobulin is four residues downstream at position 48. A precursor of these proteins, PBP, has been shown to share the first ten residues of CTAP-III, but its amino terminus is nine residues upstream at position 35. All known structural information on these three proteins fits exactly the amino acid sequence derived from the coding cDNA clone, providing strong evidence for a single precursor for all three proteins.

Thus, the 34 amino acid leader sequence of CTAP-III shown in FIG. 5 is exceptionally long, differs from classical signal peptides, and is probably responsible for targeting the protein to the α-granules of maturing megakaryocytes.

We claim:

1. A peptide having human neutrophil leukocyte-activating activity and the following amino acid sequence

| 1 | | | | 5 | | | | 10 | |
|---|---|---|---|---|---|---|---|---|---|
| X—Ala—Glu—Leu—Arg—Cys—Met—Cys—Ile—Lys—Thr— | | | | | | | | | |

| 11 | | | | 15 | | | | 20 | |
|---|---|---|---|---|---|---|---|---|---|
| Thr—Ser—Gly—Ile—His—Pro—Lys—Asn—Ile—Gln— | | | | | | | | | |

| 21 | | | | 25 | | | | 30 | |
|---|---|---|---|---|---|---|---|---|---|
| Ser—Leu—Glu—Val—Ile—Gly—Lys—Gly—Thr—His— | | | | | | | | | |

| 31 | | | | 35 | | | | 40 | |
|---|---|---|---|---|---|---|---|---|---|
| Cys—Asn—Gln—Val—Glu—Val—Ile—Ala—Thr—Leu— | | | | | | | | | |

| 41 | | | | 45 | | | | 50 | |
|---|---|---|---|---|---|---|---|---|---|
| Lys—Asp—Gly—Arg—Lys—Ile—Cys—Leu—Asp—Pro— | | | | | | | | | |

| 51 | | | | 55 | | | | 60 | |
|---|---|---|---|---|---|---|---|---|---|
| Asp—Ala—Pro—Arg—Ile—Lys—Lys—Ile—Val—Gln— | | | | | | | | | |

| 61 | | | | 65 | | | | 70 | |
|---|---|---|---|---|---|---|---|---|---|
| Lys—Lys—Leu—Ala—Gly—Asp—Glu—Ser—Ala—Asp, | | | | | | | | | | wherein X is H, Asp-Leu-Tyr-, Ser-Asp-Leu-Tyr- or Asp-Ser-Asp-Leu-Tyr-, said peptide being in a state of purity such that there is a single peak at 226 nm after chromatography on a phosphocellulose column equilibrated and washed with a pH 7.2, 20 mM potassium phosphate buffer containing 20 mM sodium chloride, 1 mM ethylenediaminetetraacetic acid and 5% glycerol using a 0.02 to 1.5M linear sodium chloride gradient eluant followed by reversed-phase high pressure liquid chromatography on, first, a C4 column using a 0% to 80% acetonitrile in 0.1% trifluoroacetic acid gradient eluant, second, a CN-propyl column using a 0% to 80% acetonitrile in 0.1% trifluoroacetic acid gradient eluant and, third, a C4 column using a 0% to 80% acetonitrile in 0.1% trifluoroacetic acid gradient eluant.

2. A peptide according to claim 1 wherein X is H.

3. A peptide according to claim 1 wherein X is Asp-Leu-Tyr-.

4. A peptide according to claim 1 wherein X is Ser-Asp-Leu-Tyr-.

5. A peptide according to claim 1 wherein X is Asp-Ser-Asp-Leu-Tyr-.

6. A pharmaceutical composition comprising a peptide according to claim 1 and a acceptable carrier.

7. A composition according to claim 6 wherein X is H.

8. A composition according to claim 6 wherein X is Asp-Leu-Tyr-.

9. A composition according to claim 6 wherein X is Ser-Asp-Leu-Tyr-.

10. A composition according to claim 6 wherein X is Asp-Asp-Leu-Tyr-.

* * * * *

UNITED STATES PATENT AND TRADEMARK OFFICE
CERTIFICATE OF CORRECTION

PATENT NO. : 5,759,533
DATED : June 2, 1998
INVENTOR(S) : Marco Baggiolini, Kenneth John Clemetson, Alfred Walz It is certified that error appears in the above-identified patent and that said Letters Patent is hereby corrected as shown below:

In the claims, claim 6 should read:

6. A composition comprising a peptide according to claim 1 and a pharmaceutically acceptable carrier.

Signed and Sealed this

Fifteenth Day of September, 1998

Attest:

BRUCE LEHMAN

Attesting Officer

Commissioner of Patents and Trademarks